United States Patent [19]
Adell

[11] Patent Number: 5,370,532
[45] Date of Patent: Dec. 6, 1994

[54] APPARATUS AND METHOD RELATING TO FACE BOWS

[75] Inventor: Loren S. Adell, 200 Adell Blvd., Sunnyvale, Tex. 75182

[73] Assignees: Loren S. Adell; Michael Adell, Sunnyvale, Tex.

[21] Appl. No.: 48,917

[22] Filed: Apr. 19, 1993

Related U.S. Application Data

[63] Continuation-in-part of Ser. No. 851,921, Mar. 16, 1992, Pat. No. 5,203,351.

[51] Int. Cl.[5] ............................ A61C 3/00
[52] U.S. Cl. ........................................ 433/5
[58] Field of Search ........................... 433/5

[56] References Cited

U.S. PATENT DOCUMENTS

| | | | |
|---|---|---|---|
| 3,311,978 | 4/1967 | Haas et al. | 433/5 |
| 3,340,613 | 9/1967 | De Woskin | 433/5 |
| 4,212,637 | 7/1980 | Dougherty et al. | 433/5 |
| 4,245,984 | 1/1981 | Hamill, Jr. | 433/5 |
| 4,881,896 | 11/1989 | Bergersen | 433/5 |

FOREIGN PATENT DOCUMENTS

2661326  10/1991  France ............. 433/5

*Primary Examiner*—John J. Wilson
*Attorney, Agent, or Firm*—George L. Boller

[57] ABSTRACT

A face bow wherein injection-molded plastic is used to form the joint between an outer bow and an inner arch. The outer bow also contains a plastic coating that provides a desired color other than that of bare metal which it covers. A clear-coat layer may also be applied over the colored layer. The plastic coating of the outer bow and the injection-molded plastic that forms the joint may have the same color.

13 Claims, 6 Drawing Sheets

APPARATUS AND METHOD RELATING TO FACE BOWS

REFERENCE TO A RELATED APPLICATION

This application is a continuation-in-part of my pending U.S. patent application Ser. No. 07/851,921, filed Mar. 16, 1992 now U.S. Pat. No. 5,203,351.

FIELD OF THE INVENTION

This invention relates to intra-oral devices, including orthodontic and mouthguard devices.

BACKGROUND AND SUMMARY OF THE INVENTION

One type of intra-oral device is a mouthguard. Examples of mouthguards are described in the Applicant's U.S. Pat. Nos. 4,955,393 and 5,082,007. Such mouthguards are fabricated by injection molding in injection molding apparatus, and they can be either consumer products sold through commercial outlets, such as department stores, sporting goods stores, etc., or they can be medical devices available through medical professionals. In some instances, the user of the mouthguard may benefit by having certain modifications made to the manufactured mouthguard so that the mouthguard is thereby customized to the individual.

In one respect, the present invention relates to apparatus and method for customizing a generically produced mouthguard for an individual user. Such method and apparatus involve the use of a manually operated electric heating gun which progressively melts the forward end of a stick of customizing material and is manipulated to apply the melted material to a generic intra-oral device in a desired manner. Where the intra-oral device is a mouthguard made of a material such as ethylene-vinyl-acetate copolymer (EVA), the stick of material is also advantageously EVA. Where the intra-oral device is a different material, such as metal, the use of an EVA stick is still advantageous because it has a certain tenacity for most materials including metals. Because the customized device is to be put to intra-oral usage, the EVA is a pharmaceutical grade of material.

The sticks are themselves novel because of unique arrangements of different zones of material constituting the sticks. For example, one stick may have one zone of one durometer material and another zone of different durometer material. In two disclosed embodiments, the zones may be either concentric or side-by-side as viewed in transverse cross-section through the sticks.

Certain features of the manually operated electric heating gun are also unique. One feature is the provision of multiple barrels for simultaneously feeding multiple sticks through the gun to a common heating chamber and dispensing nozzle. This allows one stick to be of one durometer material and another to be of a different durometer material. Another feature of the gun is a system of interchangeable nozzles which provide different patterns for the melted material being dispensed. The gun and nozzles are also provided with quick-attach and quick-release features.

Certain mouthguards have an integral attaching strap that allows the mouthguard to be attached to a face bar or mask, such as commonly used by participants in certain sports activities, and a further aspect of the present invention relates to a container for such a mouthguard. The container is selectively operable to an open condition allowing the mouthguard body to be disposed in the container. It is also selectively operable to either of two closed conditions depending upon whether or not the attaching strap has also been disposed in the container. If the attaching strap has been allowed to pass outwardly from the container, the container is operable to the first of the two closed conditions. This allows the container to be effectively used while the mouthguard remains attached to a face bar, or mask, by its attaching strap. If on the other hand the attaching strap is unattached and disposed entirely inside the container, the container can then be operated to the second of its two closed conditions, thereby completely enclosing the entirety of the mouthguard including the attaching strap.

Another type of device to which certain principles of the invention relates is an orthodontic device which has an intra-oral portion and an extra-oral portion. This device is commonly referred to as a face bow. While various configurations of face bows are commercially available, a face bow may be generically described as comprising an outer bow and an inner arch. In one type of face bow, the outer bow is a single formed wire and the inner arch is also a single formed wire. The two wires are joined by solder. In other types of face bows, more than two wires are used. They are however still soldered together. Soldering of the face bow wires is usually labor intensive, requiring a significant amount of manual processing.

In one respect, certain principles of the present invention relate to a new and improved means and method for joining face bow wires in a way that produces a better product in a more cost-effective manner. Briefly, these principles comprise joining metal face bow wires through the medium of injection molding suitable material around the wires where they are to be joined. The injection-molded material creates the joining.

The face bow wires are typically bare metal, and a recent effort to improve the cosmetic appearance of at least the extra-oral portion of face bows has involved painting the extra-oral portions of the metal wires. Painting of bare metal requires certain procedures to assure the proper adhesion of the paint, but even at that, experience has shown that the paint tends to separate for any of a number of reasons. This can lead to an unsightly appearance, and dissatisfaction with the face bow appliance.

Another aspect of the present invention relates to the processing of face bow wires in an manner that can provide better performing coloration of face bow wires. Specifically, this aspect involves the extrusion, or co-extrusion, of one, or more, lamina onto the wire that forms the face bow. The provision of extruded, or co-extruded, lamina on the metal wire is believed to provide a coloration that is more resistant to separation than painting. Moreover, it is believed that this coloration can be applied more cost-effectively than painting. It has the further advantage of being fully compatible with the uniting of plural face bow wires by means of the injection molding procedure that was described above.

The foregoing, along with additional features, advantages, and benefits of the invention, will be seen in the ensuing description and claims which should be considered in conjunction with the accompanying drawings. The drawings illustrate a presently preferred embodiment of the invention according to the best mode con-

DESCRIPTION OF THE PREFERRED EMBODIMENT

FIGS. 1-5 illustrate an exemplary mouthguard container 30 of the present invention by itself. The container comprises two separate parts 32, 34 which cooperatively form an enclosure that is generally rectangular in shape. Each part 32, 34 is in the general form of a half-shell, and when they are closed, they fit together in a telescopic manner at mating margins 36, 38. Margin 38 of part 34 is slightly indented so that when the two parts are closed together, their exteriors are generally flush with margin 36 fitting snugly over margin 38.

At the front of part 34, margin 38 is centrally provided with a rectangular notch 40 that extends downwardly from the upper edge of the margin. There are two smaller notches 42, 44 disposed spaced apart from and to either side of notch 40. Directly below the indented margin 38, part 34 contains an upwardly open rectangular pocket 46. At the front of part 32, a rectangular tongue 48 projects downwardly from margin 36. Tongue 48 is adapted to be received in pocket 46 when the two parts 32, 34 are in the second of two closed positions, to be subsequently explained.

Immediately to each side of notch 40 are two pairs of slots 50, 52. The slots 50 are the upper slots, and the slots 52 are the lower slots. Slots 50 are horizontally aligned with each other while slots 52 are horizontally aligned with each other. Immediately to each side of tongue 48, margin 36 contains a pair of ribs 54 which are horizontally aligned with each other. When the two parts 32, 34 are aligned, as in FIG. 1, and then telescoped together, as in FIGS. 2 and 3, ribs 54 first lodge in slots 50 (FIG. 2), and then in slots 52 (FIG. 3).

Figure 1:
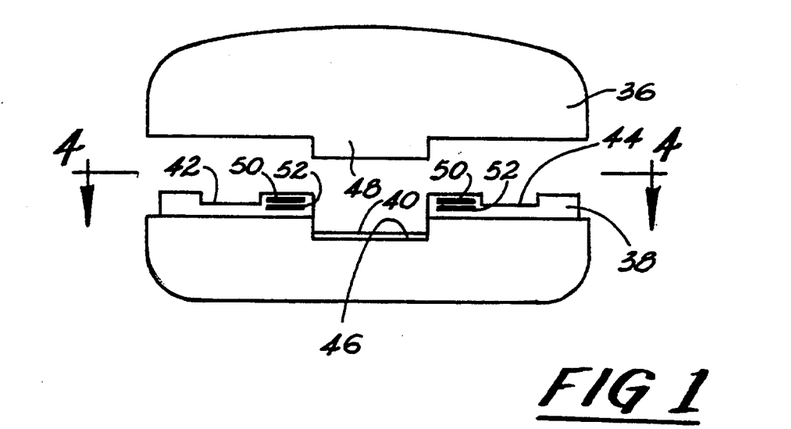
FIG. 1 is a front elevational view of a mouthguard container in accordance with principles of the invention and illustrating a partially open condition.
Figure 2:
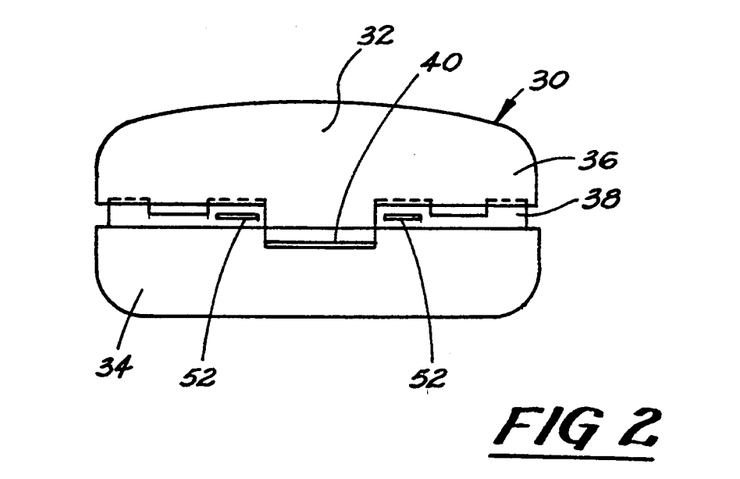
FIG. 2 is a view in the same direction as FIG. 1 illustrating a first closed condition.

The position of FIG. 2 represents a first closed position of parts 32, 34. In this position, none of notches 40, 42, or 44 is occluded by margin 36, although the two margins 36, 38 partially telescopically overlap with an interference fit. The amount of notch 40 that is not occluded is an area that is just slightly larger than the transverse cross-section of an attaching strap of a mouthguard with which container 30 can be used.

Figure 3:
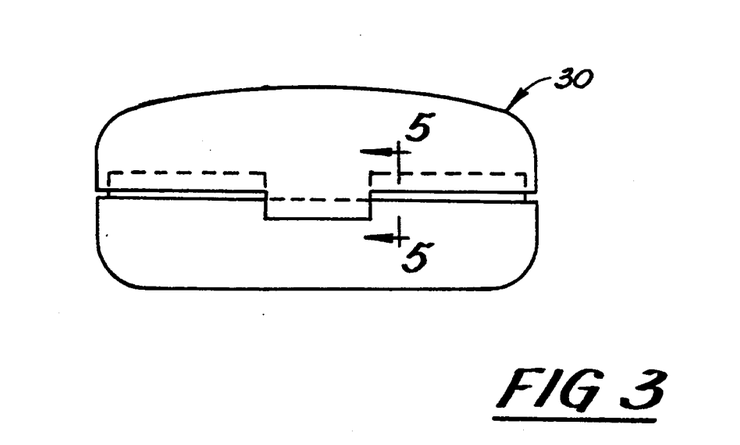
FIG. 3 is a view in the same direction as FIG. 1 illustrating a second closed condition.

The position of FIG. 3 represents a second closed position of parts 32, 34. In this position, all notches 40, 42, and 44 are occluded by margin 36, and tongue 48 lodges in pocket 46.

Figures 4, 5, 6:
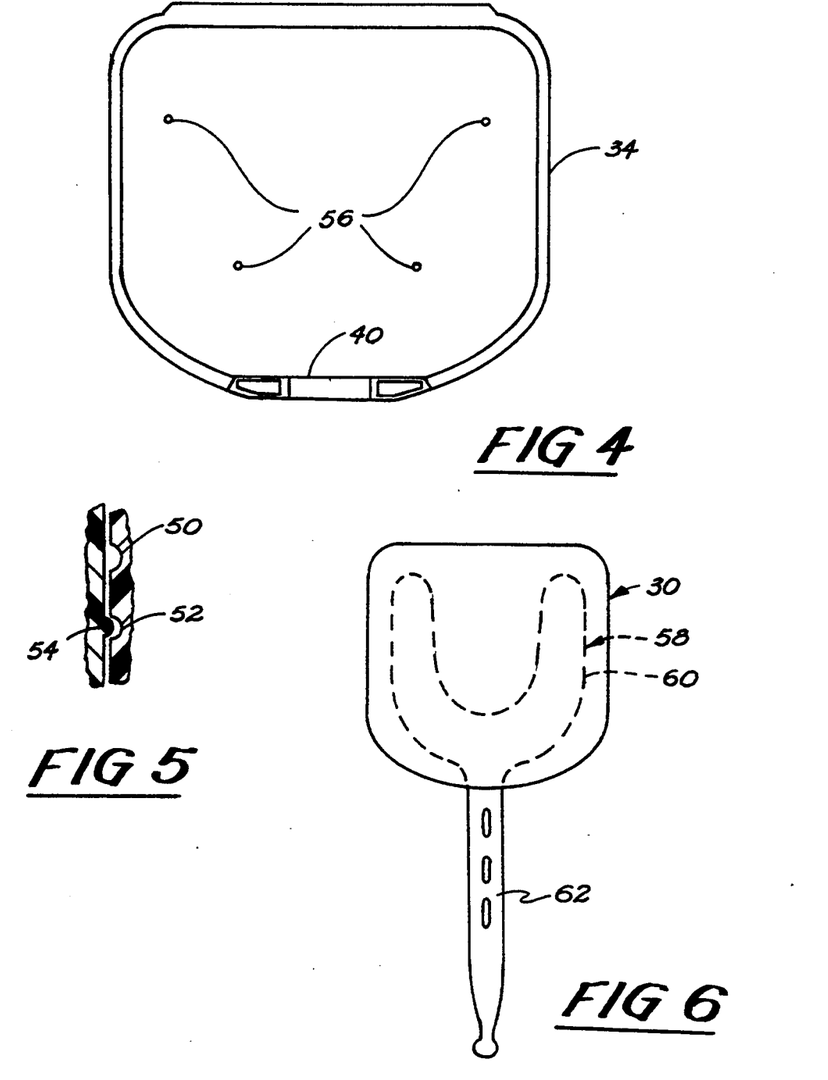
FIG. 4 is a top plan view in the direction of arrows 4—4 in FIG. 1.
FIG. 5 is an enlarged fragmentary view as taken in the direction of arrows 5—5 in FIG. 3.
FIG. 6 is a top plan view of FIG. 2, including a mouthguard.

Parts 32, 34 are fabricated from a suitable plastic that is fairly rigid, but nonetheless slightly resilient so that the two parts can be telescoped together with a modest amount of force to snap-catch ribs 54 in slots 50 or 52 depending upon which of the two closed positions the parts 32, 34 are operated to, and so that the two parts can be separated to open the container. In this regard, tongue 48 is useful in flexing the front of part 32 for disengaging ribs 54 from slots 50 and 52 when the container is to be opened. As shown in FIG. 4, the bottom wall of part 34 contains several small vent holes 56.

The two parts 32, 34 are sized to provide an enclosure for the U-shaped body of a mouthguard of the type disclosed in the aforementioned patents. Such mouthguards may also have a flexible attaching, or tethering, strap extending forwardly from the front of the U-shaped body.

Figure 7:
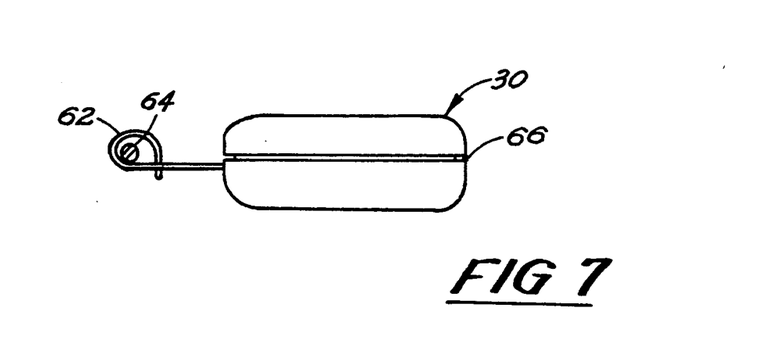
FIG. 7 is a view like FIG. 6 showing the mouthguard's attaching strap attached to a face bar, but with a slightly modified form of container.

FIG. 6 illustrates such a mouthguard 58 having such a body 60 and attaching strap 62. Body 60 is wholly contained within the enclosure that is cooperatively defined by parts 32, 34. Container 30 is shown in FIG. 6 to be in the first closed position described above. Accordingly, strap 62 can pass outwardly from the container through the non-occluded area of notch 40 so as to leave a distal end portion of the strap available for attachment to an object such as a face mask, or face bar. FIG. 7 shows such an attachment wherein the face bar is designated by the numeral 64. The distal end of the strap is configured in a conventional configuration to allow it to be looped around the face bar and back unto itself to create a tethering loop surrounding the face bar.

The advantages of the container can now be more fully appreciated. The mouthguard can be attached by its tethering strap to the face bar, and used by the individual user. When the use ceases, the container can be placed onto the main body of the mouthguard thereby enclosing the main body while allowing the strap to pass through. When the tethered mouthguard is to be used once again, the container is simply removed. Thus, the container may be used to cover the intra-oral portion of the mouthguard (i.e. the main body), while the mouthguard remains tethered to the face bar.

If the attaching strap is looped back onto the main body, the container can wholly enclose both the main body and the attaching strap and be operated to either the first or the second closed position. When in the second closed position, vent holes 56 remain unoccluded. The container of FIG. 7 differs from the one of FIGS. 1–6 in that the two parts 32, 34 are joined by an integral living hinge 66 at the rear, and hence the two parts 32, 34 open and close in clamshell fashion. Container 30 is fabricated by conventional molding procedures in suitably designed molds, such as by injection molding. The container has the further advantage that it can be used for a mouthguard which has an attaching strap and also one that does not. Because of this, it is unnecessary to have different containers for mouthguards depending upon whether or not the mouthguard has an attaching strap. The container is sized to accommodate a strap that is looped back into the container, such as by making a loop in the distal end of the strap and then folding the loop back over the front of the mouthguard to nest the loop within the U-shape of the mouthguard.

Figure 8:
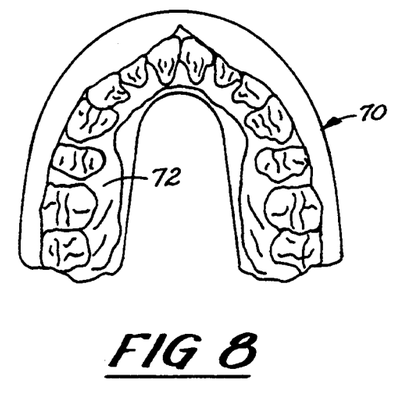
FIG. 8 is a top plan view of a mouthguard by itself.
Figure 9:
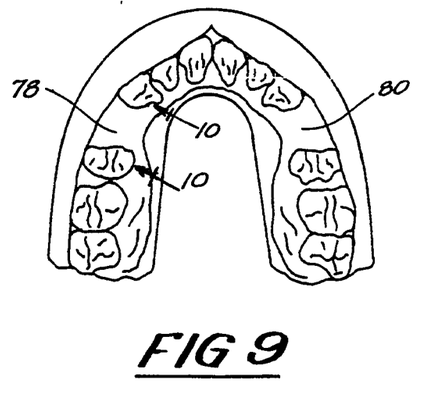
FIG. 9 is a top plan view of another mouthguard by itself.
Figures 10, 11, 12, 13, 14, 15, 16:
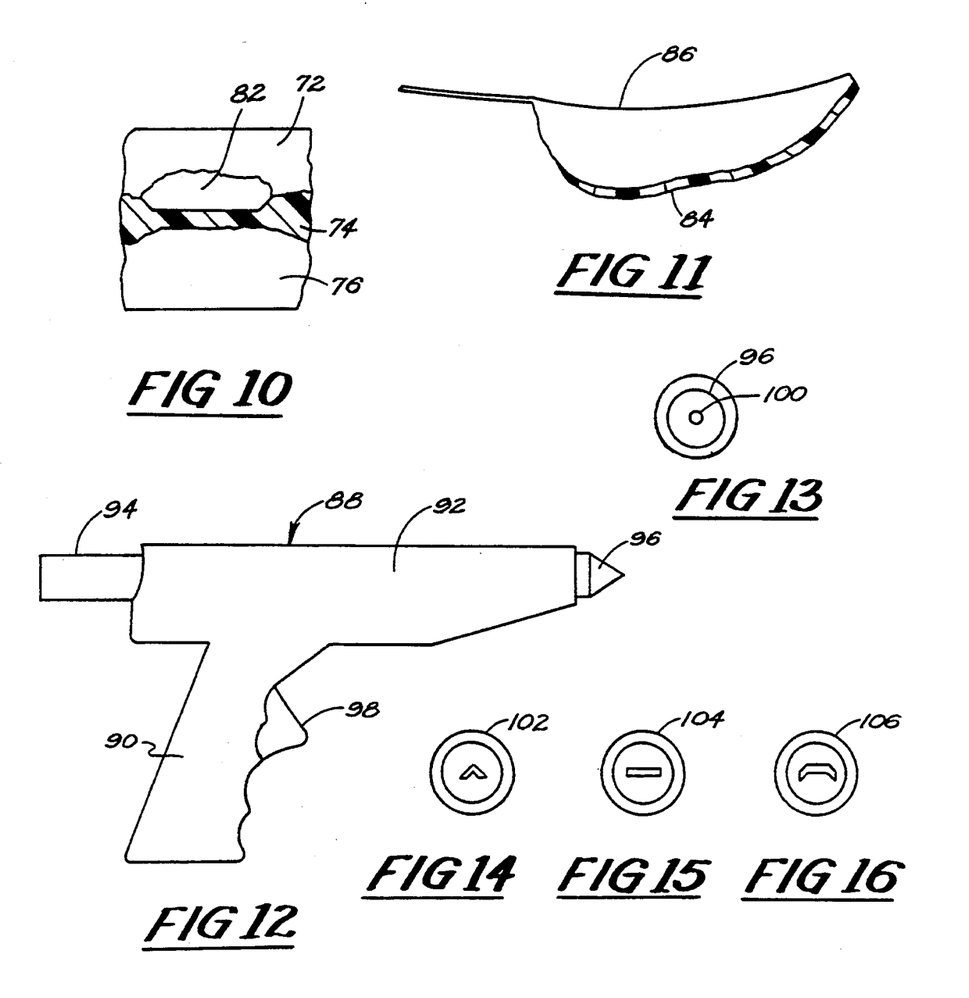
FIG. 10 is a fragmentary sectional view in the direction of arrows 10—10 in FIG. 9 showing a step in the method principles of the invention having been applied to the mouthguard.
FIG. 11 is a perspective view, with a portion in cross-section, of a dental impression tray that has been modified in accordance with method principles of the invention.
FIG. 12 is a side elevational view of a tool that is used in the practice of the method, the tool being a manually operated electric powered gun.
FIGS. 13-16 are front end views of various nozzles that are used with the tool of FIG. 12.

FIG. 8 shows a mouthguard 70 having an upper trough 72 that shares a common occlusal wall 74 with a lower trough 76. This mouthguard is like those shown in the referenced patents, and has been put to use such that impressions of the upper and lower dental arches of the user have been impressed into the respective troughs. This mouthguard represents an example where the user has a full set of teeth in the upper arch. FIG. 9 is like FIG. 8 but shows a condition where the user is missing certain teeth of the upper arch so that gaps 78 and 80 exist in the impressions as indicated. A method aspect of the invention relates to the use of a tool to add material to the mouthguard for filling these spaces at least to a certain extent. A filling 82 of gap 78 is shown in FIG. 10. The filling material is the same as that of the mouthguard, EVA in the example. The filling forms a bond with the mouthguard without the need to use separate adhesive. The filling is a hot melt material that is applied by a manually operated electric gun, to be described in connection with FIGS. 12–23.

The method is also useful for customizing intra-oral devices other than mouthguards, including for example a dental impression tray, even though the tray is metal, rather than EVA. Application of a bead 84 of hot melt material to the rim of a metal impression tray 86 is depicted by FIG. 11. A TMJ splint is an example of another intra-oral device that can be customized by principles of the invention. Such a device may require a rise from canine to canine on the lower arch. Such a rise may be created by applying hot melt material to such a splint.

FIGS. 12 and 13 illustrate a manually operated electric gun 88 for dispensing hot melt material. The gun comprises a pistol grip portion 90 and a barrel portion 92. Barrel portion 92 comprises a barrel that has an entrance at the rear for a stick 94 of hot melt material. The barrel extends forwardly to a nozzle 96 at the front end. Internally and toward the front of barrel portion 92, gun 88 contains a heating chamber that is electrically energized for melting the forward end of stick 94. The gun includes an electric cord and plug (not shown) that provides for the gun to be plugged into a standard electrical receptacle to heat its heating chamber. Pistol grip portion 90 contains a trigger 98 that operates an internal mechanism for progressively advancing stick 94 within barrel portion 92 by repeated squeezing of the trigger. This internal mechanism and the heating chamber are like those of commercially available glue guns that are used to dispense hot melt adhesive. The gun functions, as trigger 98 is squeezed, to dispense the hot melt material that has been melted from the front end of stick 94 in its heating chamber through an opening of nozzle 96. The gun is manipulated by its user to dispense the appropriate amount of hot melt material in the appropriate location so as to develop the desired shape for the modification that customizes the intra-oral device to the requirement of the particular individual user of the intra-oral device.

Nozzle 96 has a circular outlet hole 100 through which the hot melt material is dispensed. FIGS. 14, 15, and 16 depict other nozzles 102, 104, 106 that have other unique shapes for their outlets. These enable the person making the modification to develop various shapes for the hot melt material being dispensed. The nozzles are interchangeable on gun 88, preferably by the quick-attach, quick-release mechanism that will be subsequently described in connection with FIG. 23.

Figure 17:
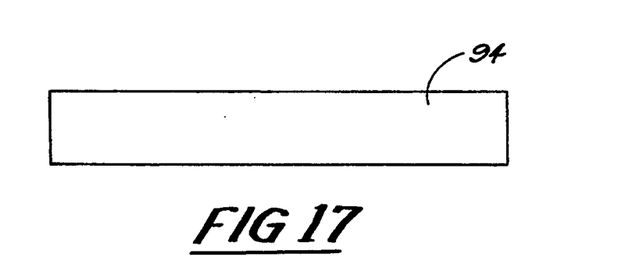
FIG. 17 is a side view of a stick of material that is used with the tool.
Figure 18:
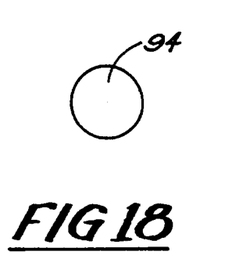
FIGS. 18-20 are end views of different forms of sticks.

FIGS. 17 and 18 show stick 94 by itself. It is a cylinder that is homogenous throughout. Because of the intra-oral usage of the modified devices, the material of stick 94 is a pharmaceutical grade, preferably EVA, as mentioned earlier. Because mouthguards fabricated of EVA are often fabricated with a fragrance additive, stick 94 may be similarly fragranced with a fragrance additive.

Sticks 94 may be manufactured by a process of extrusion in an extruder. The sticks are cut to length from the extruded material.

Figure 19:
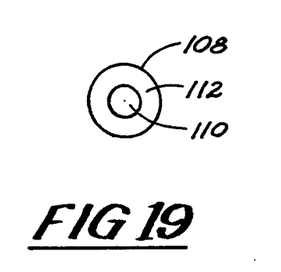

FIG. 19 depicts a stick 108 which has a central cylindrical core 110 that is surrounded by a cylindrical sleeve 112. The two are of the same material but of different durometers. Such a stick is fabricated by first extruding core 110, and then extruding sleeve 112 onto core 112.

Figure 20:
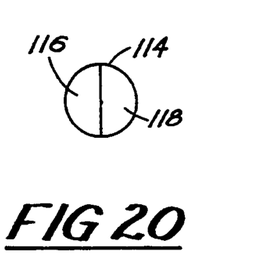

FIG. 20 depicts yet another stick 114 which has two hemispheres 116, 118 of the same material but of different durometers. This stick is fabricated by co-extruding the two hemispheres simultaneously, or it could be fabricated by first extruding one hemisphere and then extruding the other hemisphere onto the first.

Figure 21:
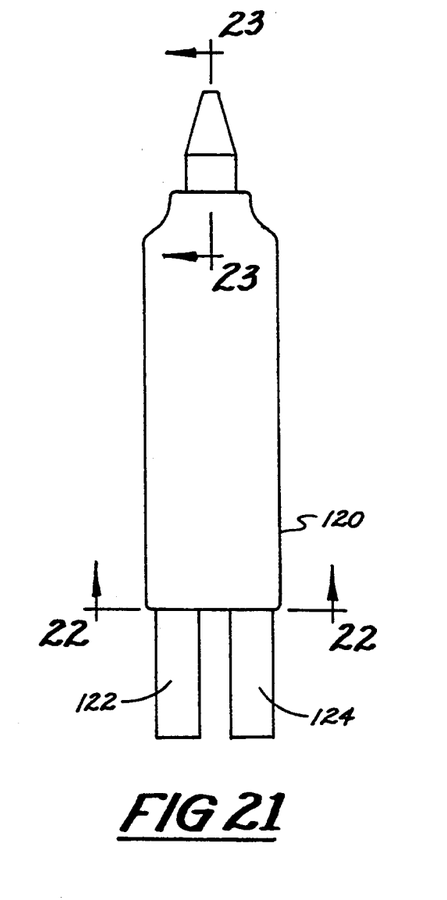
FIG. 21 is a top plan view of another embodiment of tool.
Figure 22:
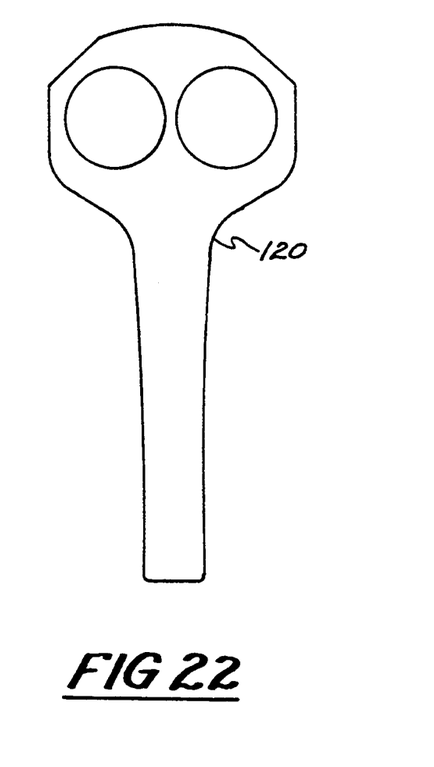
FIG. 22 is a rear elevational view in the direction of arrows 22—22 in FIG. 21.

FIGS. 21 and 22 illustrate another form of gun 120. This gun is like the first except that it has two separate barrels via which respective sticks 122, 124 can be fed. The barrels share the common heating chamber at the forward end of the barrel portion so that the melted material from the front end of one stick mixes with that from the other before the mixture is dispensed from the nozzle. This embodiment of gun can have the same effect as the use of a dual durometer stick 108, 114 in the single barrel gun 88. This is accomplished by feeding a stick of one durometer in one barrel and a stick of different durometer in the other barrel.

Figure 23:
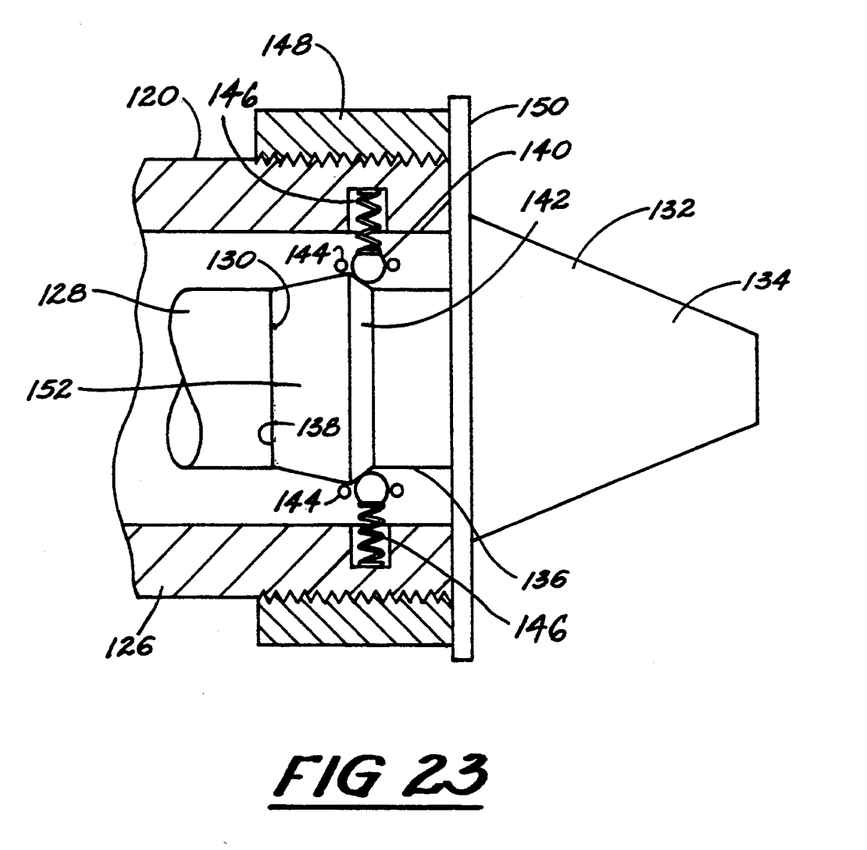
FIG. 23 is a fragmentary enlarged cross-sectional view in the direction of arrows 23—23 in FIG. 21 showing additional details.

FIG. 23 shows a quick-attach, quick-release mechanism for the nozzles. The forward end of the gun barrel portion comprises an outer body 126 surrounding the heating chamber 128 in which the forward end of a stick of hot melt material is melted. The forward end of heating chamber 128 terminates in a finished transverse surface 130. The nozzle 132 has a forwardly disposed dispensing tip 134 and a tubular shank 136 extending rearwardly from tip 134. Shank 136 terminates rearwardly in a finished transverse surface 138 that forcefully abuts surface 130 to form a seal between the two which provides for melted material to pass from heating chamber 128 into and through nozzle 132 for dispensing from tip 134. FIG. 23 shows the installed position of the nozzle on the gun. The forceful abutment of surface 138 with surface 130 is attained by the engagement of a plurality of spring-loaded balls 140 with a frusto-conically tapered surface 142 of shank 136. Balls 140 are arranged at uniform intervals around a circular cage 144 that is retained on outer body 126 in surrounding relation to shank 136. Springs 146 act on balls 140 to urge them radially inwardly. The reaction of the balls with surface 142 forces the nozzle toward the rear of the barrel thereby forcing surface 138 against surface 130.

Release of the nozzle from the barrel is accomplished via a large nut 148 that is threaded onto an exterior thread on outer body 126. The nut is twisted in a direction that causes the nut to move forwardly on the outer body. The forward face of the nut engages a flange 150 of nozzle 132, and continued twisting of the nut pushes the nozzle forwardly relative to outer body 126 against the opposite component of force exerted by balls 140 on surface 142. Eventually a point is reached where the balls clear surface 142, freeing the nozzle.

The removed nozzle can be replaced by a different one by twisting nut 148 to sufficiently retract it on the barrel so that it will not interfere with the flange 150 of the new nozzle. The new nozzle is installed by inserting its shank 136 into the open forward end of the barrel. Rearwardly of surface 142, shank has an oppositely tapered frusto-conical surface 152 that has a shallower taper than surface 142. As the nozzle is being inserted into the barrel, surface 152 engages balls 140, retracting them against the spring forces. When the balls clear surface 152, the spring forces are exerted on surface 142, causing the nozzle to snap into place with surfaces 138 and 130 forcefully abutting.

Figure 24:
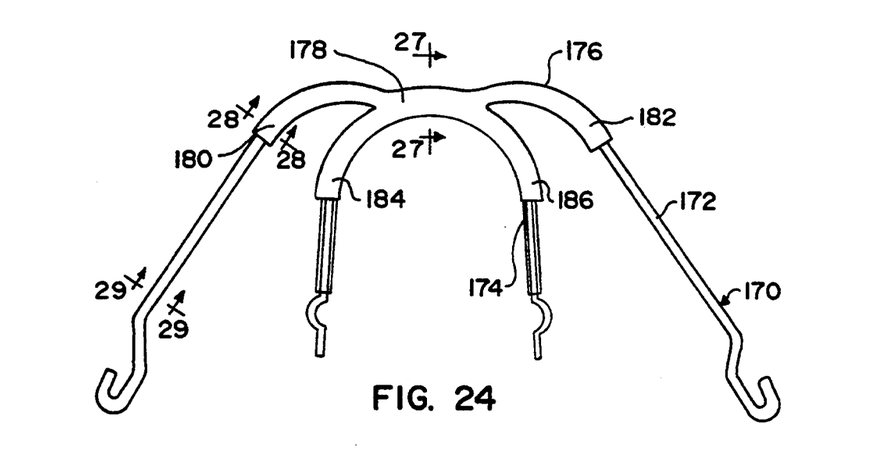
FIG. 24 is a top plan view of an example of a face bow embodying certain principles of the invention.

FIGS. 24-31 relate to a face bow embodying certain principles of the invention. A complete embodiment of an example of a face bow is shown in FIG. 24 and identified by the numeral 170. It comprises an outer bow 172 and an inner arch 174. In accordance with this aspect of the invention, an injection-molded cap 176 is cooperatively associated with outer bow 172 and inner arch 174. Cap 176 is a suitable injection-molded material, certain polymers and/or co-polymers being suitable materials.

Figures 25, 26:
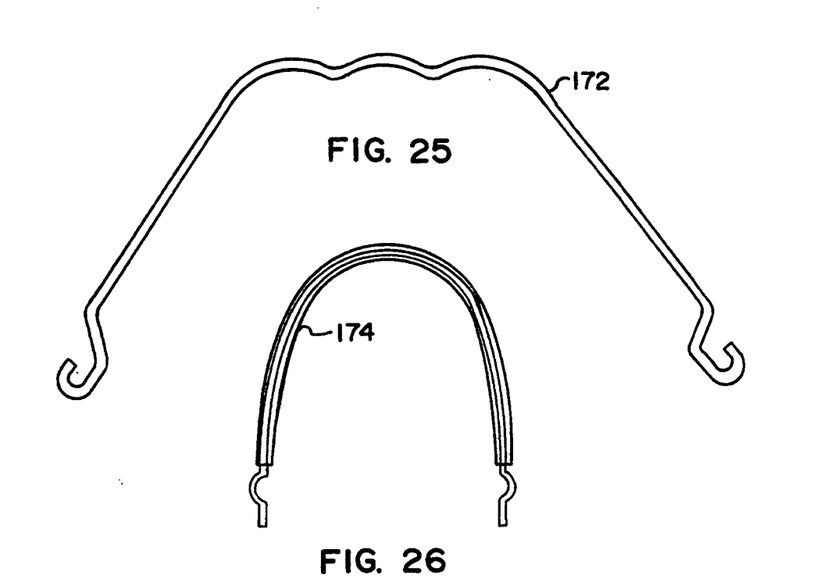
FIG. 25 is a top plan view of one of the parts of the face bow by itself.
FIG. 26 is a top plan view of another of the parts of the face bow by itself.

Outer bow 172 is a bare metal wire of suitable characteristics for its intended use. Likewise inner arch 174 is bare metal of suitable characteristics for its intended use. Typically outer bow 172 is a single piece of solid circular cross-section, as shown. Inner arch 174 may be a circular metal tube into whose opposite ends loop-containing wires are inserted and joined. The shapes to which the individual outer bow 172 and individual inner arch 174 are formed, as shown by FIGS. 25 and 26, are conventional. At and immediately adjacent the mesial plane, outer bow 172 is shaped to allow a segment of inner arch 174 that spans the mesial plane to coalesce with it. In prior face bows, the two parts were then soldered together along these segments. Such a process typically requires a significant amount of labor to perform so that an acceptable finished product results. The joint between the two parts must be carefully made so that they are properly united and so that the finish is smooth and free of sharp edges and pitting. The resulting appearance of the finished face bow is that of a single bare metal part, although it is actually more than one wire joined together.

The present invention is intended to accomplish joining of an outer bow and an inner arch in a novel manner that provides certain benefits over the prior process. Thus, cap 176 serves to join the outer bow and inner arch so that the soldering can be eliminated. According to the invention, outer bow 172 and inner arch 174 are placed together in an injection mold such that material that is to form cap 176 can be injection-molded around them to create the shape shown in the Figs. After the injection-molded cap has solidified, the completed face bow is removed from the mold.

Figure 27:
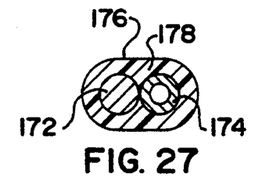
FIG. 27 is an enlarged transverse cross-section taken along line 27—27 in FIG. 24.
Figure 28:
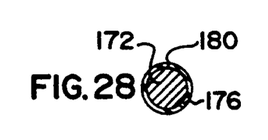
FIG. 28 is an enlarged transverse cross-section taken along line 28—28 in FIG. 24.
Figure 29:
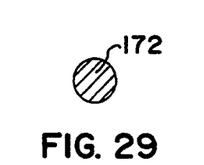
FIG. 29 is an enlarged transverse cross-section taken along line 29—29 in FIG. 24.

The cap spans segments of outer bow 172 and inner arch 174 to each side of the mesial plane. At and immediately proximate the mesial plane, cap 176 has a core 178 that commonly encloses the coalescing parts 172, 174, as shown by FIG. 27. More distally, the cap comprises individual branches 180, 182, 184, and 186. Branches 180 and 182 extend along outer bow 172, and branches 184 and 186, along inner arch 174. A representative cross-section is shown in FIG. 28 where it can be seen that the branches have circular cross-sections, each of uniform thickness.

The material used to create cap 176 must be injection-moldable, and it must be sufficiently rigid, when cured, that it securely holds outer bow 172 and inner arch 174 in the desired assembly relationship that enables the proper vectors to be developed when the face bow is applied to a patient being treated. The material must allow the branches to flex slightly about core 178 as the portions of the metal parts which the branches cover undergo limited flexing when the face bow is used. Polycarbonate is a very suitable material for cap 176, either glass-filled, or unfilled. Other materials include urethanes, ABS, and polypropylene. These materials can be molded to the required dimensions and present a suitable finish appearance directly from the mold so that further processing is unnecessary.

It should be observed that the core 178 and the branches 180, 182, 184, and 186 of cap 176 extend along segments of parts 172 and 174 that have a noticeable amount of curvature. This is helpful in strengthening the joint because of the large resistance that is imparted by a similar curvature of the cap. For securing the best quality in the joint, full adherence of the injected material to the parts 172 and 174 should be sought, and this can be accomplished by proper treatment of the parts 172, 174 before they are placed in the mold. It is possible that an injected material may have sufficient tenacity to bond directly to parts 172, 174, but in some cases adhesive may be used to enhance the adherence.

The injected material may also be colored so that in the finished face bow, cap 176 presents a desired color. Such coloration is often considered a desirable attribute in orthodontic devices from the standpoint of appearance and/or acceptance of a device by a patient. At the present time, it is a practice to paint outer bows with paint of a desired color. Unfortunately, experience has shown that the painting tends to rather rapidly come off, especially where the face bow is used by a child. Since color can be inherently imparted to cap 176 without a subsequent painting step, the use of an injected-molded cap of a desired color is believed significantly better than merely painting a metal face bow. Accordingly, it would be possible to injection-mold material onto a greater extent of the face bow than is shown by FIG. 24. However, there is another way of creating a face bow that is more extensively colored. That is by applying a coating of colored material to the wire by an extrusion, or co-extrusion process.

Figure 30:
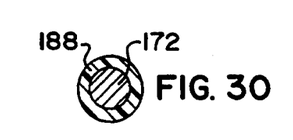
FIG. 30 is a view similar to FIG. 29 showing a modified form.
Figure 31:
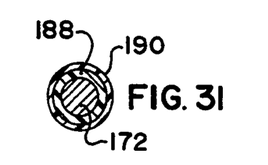
FIG. 31 is a view similar to FIG. 29 showing another modified form.

For example, the metal wire that is used to create outer bow 172 may be processed through an extrusion line that extrudes a coating of colored material onto it as shown by FIG. 30 in which the coating is designated by the numeral 188. Examples of suitable materials for extruding onto the wire are polyethylene and polyvinyl chloride. They can be bonded well to metal, and they can be colored to any of a number of different colors. Since the coated wire will come in a long length after having been processed through an extrusion line, either an individual wire for an outer bow is cut to length and then formed to the proper shape by bending, or the coated wire is shaped by a progressive die, or like operation, and then cut. A properly coated wire will allow enough bending for a face bow without delamination or separation of the coating from the metal. A wire used to form an inner arch may be processed in like manner. It and the outer bow may be placed in a mold and joined by injection molding a cap 176 over them, as described earlier. If necessary, some of the coating may be stripped from the wire since the wire will be fully enclosed as it comes from the extrusion line. While a single-layer coating like coating 188 is well-suited for a face bow, a two-layer coating like that shown in FIG. 31 may be used. In addition to the colored layer 188, there is a clear-coat overlay 190, both of which are circular. The transparent overlay 190 allows the underlying color of coating 188 to be seen while the layer 190 provides protection for it. Examples of suitable materials for overlay 190 are Primacor ™ and clear urethanes. Overlay 190 can be applied to the wire on an extrusion line after layer 188 has been extruded onto the bare metal.

The use of extrusion or co-extrusion to apply a single or a double layer coating to a face bow wire can be used independently of the use of an injection-molded cap 176 to join the two parts 172, 174. Likewise, it is possible that the two parts 172, 174 could be pre-joined by an operation like brazing, welding, or even rough soldering that does not entail the time and expense of fine finishing, and then completed by injection molding cap 176 to finish the joint. While reference has been made to the fact that parts 172, 174 are metal, principles of the invention can be used even if one or both of the parts 172, 174 are not metal. For example, part 172 could be a suitable plastic wire that has been injection-molded to desired shape from suitable material, possibly a polycarbonate or nylon that is strong, but slightly flexible. In fact, a material that is sufficiently rigid, but with slight flexibility, can be injection-molded to create one of the wires 172, 174, and cap 176 in a single operation, molding onto the other of the wires 172, 174.

While a presently preferred embodiment of the invention has been illustrated and described, it should be appreciated that principles are applicable to other embodiments.

What is claimed is:

1. A face bow comprising an outer bow that is disposed substantially extra-orally when the face bow is used and an inner arch that is disposed substantially intra-orally when the face bow is used, wherein an injection-molded cap encloses said inner arch and said outer bow at a joint that joins said inner arch and said outer bow and, wherein said outer bow comprises a colored layer of plastic and said cap has a color matching that of said colored layer.

2. A face bow as set forth in claim 1 wherein said colored layer of plastic of said outer bow is polyvinyl chloride.

3. A face bow comprising an outer bow that is disposed substantially extra-orally when the face bow is used and an inner arch that is disposed substantially intra-orally when the face bow is used, wherein said outer bow comprises a metal wire that is covered by a layer of extruded plastic material, and wherein said layer is a colored material, and further including a second layer of clear material that covers said first-mentioned layer.

4. A method of making a face bow which comprises:
passing metal wire through an extrusion line and extruding plastic onto said metal wire as it passes through the extrusion line to create plastic-coated wire and thereafter cutting the plastic-coated wire to a suitable length for forming into an outer bow of a face bow;
forming the cut length of plastic-coated wire into such an outer bow;
providing an inner arch of a face bow;
disposing a portion of the outer bow proximate a portion of the inner arch; and
joining said portions to create a joint that operatively unites said outer bow and said inner arch as a face bow capable of developing desired force vectors for an orthodontic treatment procedure.

5. A method as set forth in claim 4 in which said joining step comprises injection molding a cap onto mesial portions of said outer bow and said inner arch to create said joint.

6. A method as set forth in claim 4 in which said joining step comprises an initial joining of said portions followed by enclosing the initial joining by means of a cap.

7. A method as set forth in claim 6 in which said enclosing step is conducted by injection-molding material to create said cap in situ.

8. A method as set forth in claim 4 in which said extruding step comprises extruding polyvinyl chloride onto said metal wire to create plastic-coated wire.

9. A face bow comprising an outer bow that is disposed substantially extra-orally when the face bow is used and an inner arch that is disposed substantially intra-orally when the face bow is used, wherein said outer bow comprises a metal wire that is covered by a layer of a first plastic, said outer bow and inner arch are joined at mesial regions thereof by a joint comprising an injection-molded cap of a second plastic that in transverse cross section encloses said mesial regions, said layer of first plastic covering said outer bow is a different plastic from said second plastic of said injection-molded cap, and at least some of said first plastic extends labially of said second plastic of said cap.

10. A face bow as set forth in claim 9 wherein said first plastic and said second plastic comprise matching colors.

11. A face bow as set forth in claim 9 wherein said first plastic is polyvinyl chloride.

12. A method of making a face bow which comprises:
providing a plastic-coated straight metal wire;
forming said plastic-coated wire into an outer bow of a face bow;
providing an inner arch of a face bow;
disposing a portion of the outer bow proximate a portion of the inner arch;
joining said portions to create a joint that operatively unites said outer bow and said inner arch as a face bow capable of developing desired force vectors for an orthodontic treatment procedure; and
in which said joining step comprises injection molding a cap onto mesial portions of said outer bow and said inner arch to create said joint.

13. A method of making a face bow which comprises:
providing a plastic-coated straight metal wire;
forming said plastic-coated wire into an outer bow of a face bow;
providing an inner arch of a face bow;
disposing a portion of the outer bow proximate a portion of the inner arch;
joining said portions to create a joint that operatively unites said outer bow and said inner arch as a face bow capable of developing desired force vectors for an orthodontic treatment procedure; and
in which said joining step comprises an initial joining of said portions followed by enclosing the initial joining by means of a cap; and
in which said enclosing step is conducted by injection-molding material to create said cap in situ,

* * * * *